(12) United States Patent
Chung et al.

(10) Patent No.: US 7,575,938 B2
(45) Date of Patent: Aug. 18, 2009

(54) METHOD FOR DIAGNOSING LIVER DISEASES

(75) Inventors: Tai-Wha Chung, Daejeon (KR); Eun-Young Song, Seoul (KR); Ji-Hyun Kang, Daejeon (KR); Kyoung-A Kim, Daejeon (KR); Eun-Young Lee, Daejeon (KR); Yong-Kyung Choe, Daejeon (KR)

(73) Assignees: Neobiodigm Co., Ltd, Jinju-Si (KR); Korea Research Institute of Bioscience and Biotechnology, Yuseong-Gu (KR)

( * ) Notice: Subject to any disclaimer, the term of this patent is extended or adjusted under 35 U.S.C. 154(b) by 50 days.

(21) Appl. No.: 10/540,848

(22) PCT Filed: Dec. 27, 2003

(86) PCT No.: PCT/KR03/02860

§ 371 (c)(1),
(2), (4) Date: Mar. 29, 2006

(87) PCT Pub. No.: WO2004/058823

PCT Pub. Date: Jul. 15, 2004

(65) Prior Publication Data

US 2006/0177876 A1    Aug. 10, 2006

(30) Foreign Application Priority Data

Dec. 27, 2002    (KR) .................. 10-2002-0084834

(51) Int. Cl.
  *G01N 33/53*    (2006.01)
(52) U.S. Cl. .................. 436/514; 435/7.1; 435/7.9; 435/4; 435/7.92; 435/7.94; 530/388.1
(58) Field of Classification Search .................. 435/7.1, 435/7.9, 4, 7.92, 7.94; 530/388.1
  See application file for complete search history.

(56) References Cited

FOREIGN PATENT DOCUMENTS

| EP | 0 199 196 | 10/1986 |
|----|-----------|---------|
| WO | 98/22824 | 5/1998 |
| WO | 01/35105 | 5/2001 |
| WO | 01/35105 A1 | 5/2001 |

OTHER PUBLICATIONS

Song et al., Hepatology Research. Aug. 2003. vol. 26, No. 4, pp. 311-317. Abstract Only.*
McFarlane et al., Clinical and Experimental Immunology. Feb. 1984 vol. 55, No. 2, pp. 347-354. Abstract Only.*
Song et al., Clinical Chemistry. Jun. 2001. vol. 47, No. S6. pp. A152.*
Fraeyman et al., Clinical Chemistry. 1987. vol. 33, No. 12, pp. 2275-2277.*
Fraeyman et al., Hybridoma. 1987. Vo. 6, No. 6, pp. 565-574.*
Chinese Office Action for corresponding Chinese Patent Application No. 2003801077250 dated Aug. 17, 2007.
Indian Office Action for corresponding India patent application No. 1296/KOL-NP/2005 dated Oct. 11, 2006 (in English).
Chinese Office Action for corresponding Chinese patent application No. 2003801077250 dated Dec. 8, 2006.
Kilian Dill et al., "Detection of human asialo-$\alpha_1$-acid glycoprotein using a heterosandwich immunoassay in conjunction with the light addressable potentiometric sensor", Glycoconjugate Journal, vol. 13(4), pp. 637-641 (1996).
Fionnuala T. Lundy et al., "An Antibody—Lectin Sandwich Assay for Quantifying Protein Glycoforms", Molecular Biotechnology, vol. 12(2), pp. 203-206 (1999).
International Search Report for Application No. PCT/KR2003/002860, dated May 12, 2004.
Chinese Office Action for corresponding Chinese Patent Application No. 200380107725 dated Dec. 28, 2007.
Song et al., "Elevation of serum asialo-$\alpha_1$ acid glycoprotein concentration in patients with hepatic cirrhosis and hepatocellular carcinoma as measured by antibody-lectin sandwich assay", Hepatology Research, 2003, pp. 311-317 (in English).
Zenon Steolewski, "Hybridoma", 1987, vol. 6, p. 565-574.
Hideki Ozawa et al., Archives of Biochemistry and Biophysics, vol. 342, p. 48-57, 1997.
H. Trebeden et al., European Cytokine Network, 2001, vol. 12, p. 359-360.
Fionnuala T. Lundy et al., Molecular Biotechnology, 1999, vol. 12, p. 203-206.
Hiroyuki Iwata et al. J. Vet. Med. Sci., 2000, vol. 62, p. 1099-1100.
Japanese Office Action with English Translation, issued Jul. 1, 2008.

* cited by examiner

*Primary Examiner*—Bao-Thuy L Nguyen
(74) *Attorney, Agent, or Firm*—Staas & Halsey LLP (57) ABSTRACT

The present invention relates to a method for diagnosing a liver disease rapidly in an early stage. More particularly, the present invention relates to a monoclonal antibody against asialo $\alpha_1$-acid glycoprotein; a method for diagnosing a liver disease which evaluates asialo $\alpha_1$-acid glycoprotein in a test sample by using said monoclonal antibody; and an diagnostic strip for immunochromatography composed of said monoclonal antibody against asialo $\alpha_1$-acid glycoprotein and *Ricinus communis* agglutinin (RCA). The diagnostic device of the present invention is convenient to measure the concentration of asialo $\alpha_1$-acid glycoprotein and to diagnose a liver disease rapidly.

2 Claims, 6 Drawing Sheets
(4 of 6 Drawing Sheet(s) Filed in Color)

1 : $\alpha_1$-acid glycoprotein + heptoglobin + $\alpha_2$-macroglobulin
2 : normal person
3 : 1.5 μg/ml
4 : 2.0 μg/ml
5 : 3.0 μg/ml
6 : 4.0 μg/ml

FIG. 5

METHOD FOR DIAGNOSING LIVER DISEASES

TECHNICAL FIELD

The present invention relates to a method for diagnosing a liver disease rapidly in an early stage. More particularly, the present invention relates to a monoclonal antibody against asialo α1-acid glycoprotein; a method for diagnosing a liver disease which evaluates asialo α1-acid glycoprotein in a test sample by using said monoclonal antibody; and an diagnostic strip for immunochromatography composed of said monoclonal antibody against asialo α1-acid glycoprotein and *Ricinus communis* agglutinin (RCA). The diagnostic device of the present invention is convenient to measure the concentration of asialo α1-acid glycoprotein and to diagnose a liver disease rapidly.

BACKGROUND

Liver disease including hepatitis, liver cirrhosis, and hepatocarcinoma is the most prevalent disease in Korea, Japan, Taiwan, China and other Southeast Asian countries. Presently, liver diseases have been diagnosed by evaluating the content of bilirubin or urobilinogen from patients' urine, by measuring the contents of glutamic-oxaloacetic transaminase (GOT), glutamic pyrubic transaminase, total bilirubin, albumin, lactic acid dehydrogenase and the like so as to analyze the changes of biochemical components in blood and by detecting an antigen from hepatitis B virus (HBV) or hepatitis C virus (HCV) or antibody against these viruses. Besides, liver cirrhosis can be diagnosed by alpha-feto protein (AFP) and carcinoembryonic antigen (CEA) test. However, liver is a complex organ due to various functions and is vitally specific not to reveal an abnormal state outwardly. Furthermore, an early diagnostic method has not been established yet and thus liver disease is often difficult to be treated, since it is diagnosed after severely worsen.

The present inventors have developed a marker which diagnoses a liver disease in a early stage clinically and reflects the severity of patient exactly and then manufactured a diagnostic kit. It has been disclosed in the patent application and the treatise that the marker be a remarkable agent for diagnosing a liver disease.

Precisely, the present inventors have demonstrated the diagnostic method and the diagnostic kit in Korean patent application PCT/KR00/00840 (Aug. 1, 2000), U.S. patent application Ser. No. 09/662,363 (Sep. 13, 2000) and Korean patent application 10-2000-0040609 (Jul. 14, 2000), which exploits the sandwich ELISA method by using the specific antibody and lectin and measures asialo glycoprotein in blood. This techniques are confirmed to be recurrent and accurate and thus to be useful for diagnosing liver functions and to treat hepatic diseases.

It is reported that asialo glycoprotein represent the prognostic status of hepatic disease as a marker in blood serum (T. Sawamura et al., Gastroenterology 1981, 81: 527~533; T. Sawamura et al., Gastroenterology 1984, 87: 1217~1221). In addition, it is elucidated that asialo glycoprotein help to detect the status of hepatic cancer since the concentration is proportional to the severity in liver cancer (T. Sawamura et al., Gastrologia Japonica 1985, 20: 201~208).

Conventionally, the receptor against asialo glycoprotein is separated from human or other animal such as rabbit and mouse, purified and applied as a capture protein in order to measure the concentration of asialo glycoprotein. After it is labeled with radioactive substrates, the competitive radioactive assay and electro immunodiffusion are accomplished (J. S. Marshall et al., J. Lab. Clin. Med. 1978, 92: 30~37; N. Serbource-Goguel et al., Hepatology 1983, 3: 356~359).

Unfortunately, there are some problems. Above all, the receptor against asialo glycoprotein is difficult to be obtained in a large scale, although the test kit needs a large amount of asialo glycoprotein. In case of competitive radioreceptor assay, it is dangerous to use radioactive substance and hard to prepare special facilities for treating waste material and the like. In cases of electroimmunodiffusion, it is complicated to analyze data quantitatively. Especially, the competitive assay is not suitable for general diagnostic kit since it lacks accuracy and recurrence.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which.

DISCLOSURE OF THE INVENTION

In order to settle above-mentioned technical problems and to diagnose a liver disease rapidly and easily by detecting asialo glycoprotein, the present inventors have attempted to develop a monoclonal antibody specific for asialo α1-acid glycoprotein (AsAGP), a diagnostic method for liver disease by using said monoclonal antibody and a diagnostic strip for immunochromatography useful for the same method. As 16.89 (lymphoblast-like hybridoma cell lines), assigned accession number KCTC 10261BP, has been deposited in the Korean Collection for Type Cultures, Korea Research institute of Bioscience and Biotechnoloty (KRIBB) #52, Oundong, Yusong-ku, Taejon 305-333, Republic of Korea, as International Depositary Authority as established under the Budapest Treaty on the International Recognition of the Deposit of Microorganisms for the Purposes of Patent Procedure on May 24, 2002.

The object of the present invention is to provide a device and a method for detecting a liver disease easily.

In order to attain said object, the present invention provides a monoclonal antibody binding only with asialo α1-acid glycoprotein and excluding heptoglobin and α2-macroglobulin.

The monoclonal antibody of the present invention also does not react asialo heptoglobin and asialo α2-macroglobulin. Preferably, the monoclonal antibody of the present invention is a subclass type $IgG_1$.

The monoclonal antibody can be prepared by the process disclosed in the prior arts (Davidson R. L. and P. S. Gerald 1976, Improved techniques for the induction of mammalian cell hybridization by polyethylene glycol, Somatic Cell Genet., 2: 165~176; Knott C. L., Kuus-Reichel K., Liu R. and Wolfert R. L. 1997, Development of antibodies for diagnostic assays, In Price C. and Newman D. (eds.), Principles and Practice of Immunoassay, $2^{nd}$ ed. New York, Stockton Press, 36~64; Gillete R. W. 1987, Alternatives to pristine priming for ascitic fluid and monoclonal antibody production, J. Immunol. Meth. 99, 21~23; Norwood T. H., C. J. Zeigler and G. M. Martin 1976, Dimethyl sulphoxide enhances polyethylene glycol-mediated somatic cell fusion, Somatic cell Genet., 2: 263~270) Precisely, it is manufactured by the process which comprises (1) separating asialo α1-acid glycoprotein and (2) immunizing mice.

Above all, in order to produce the monoclonal antibody obtained above in a large scale, the hybridoma cell is prepared by the conventional process, separated, screened, injected into a mouse peritoneally and then collected from peritoneal fluid.

Concretely, asialo α1-acid glycoprotein is purified from blood by the process as described in the patent applications [PCT application PCT/KR00/00840 (Aug. 1, 2000), U.S. patent application Ser. No. 09/662,363 (Sep. 13, 2000), Korean patent application 10-2000-0040609 (Jul. 14, 2000)]. Asialo α1-acid glycoprotein is suspended by using phosphate buffer, blended by using Titer-MAX and applied to immunize a mouse. A spleen cell and a myeloma cell are separated from the experimental mouse immunized, fused and screened to select a hybridoma cell line specific for asialo α1-acid glycoprotein by ELISA method. In order to produce the monoclonal antibody specific for asialo α1-acid glycoprotein in a large scale from the hybridoma cell above, the hybridoma cell producing the monoclonal antibody against asialo α1-acid glycoprotein is injected to experimental mice and the peritoneal fluid of the mice containing the hybridoma cell in a high level is collected and separated a cell specific for the monoclonal antibody of the present invention.

In addition, the present invention also provides the hybridoma cell line which can produce in a large scale a monoclonal antibody binding only with asialo α1-acid glycoprotein excluding heptoglobin and α2-macroglobulin.

In order to investigate whether the monoclonal antibody against asialo α1-acid glycoprotein obtained from the hybridoma cell be specific for asialo α1-acid glycoprotein or not, asialo α1-acid glycoprotein is first analyzed by performing electrophoresis and western blotting. It is further examined whether the monoclonal antibody of the present invention reacts only with asialo α1-acid glycoprotein and excludes other glycoproteins by performing ELISA method and the like as demonstrated in Example 2.

Preferably, the present invention provides the hybridoma cell line, producing the subclass type $IgG_1$ monoclonal antibody specific for asialo α1-acid glycoprotein and deposited to Korea Research Institute of Bioscience and Biotechnology, Gene Bank in May 24, 2004 (accession number KCTC 10261 BP) under Budapest Treaty.

In addition, the present invention provides a method for detecting a hepatic disease which comprises steps (1) reacting a monoclonal antibody which binds only with asialo α1-acid glycoprotein and excludes heptoglobin and α2-macroglobulin; Ricinus communis agglutinin (hereinafter, referred to as "RCA") as a lectin, specifically recognizing asialo glycoprotein; and a test sample; and (2) measuring asialo α1-acid glycoprotein (AsAGP).

In the method for detecting a hepatic disease of the present invention, test samples can be analyzed on a microplate through a sandwich enzyme immunoassay, an enzyme immunoassay onto an diagnostic strip for immunochromatography and various types of enzyme immunoassay. Especially, the enzyme immunoassay onto diagnostic strip for immunochromatography is the most convenient among these methods.

Preferably, the monoclonal antibody utilized in the diagnostic method of the present invention is a subclass type $IgG_1$ as described above. More preferably, the monoclonal antibody is produced from the mouse hybridoma cell line of the present invention deposited with accession number KCTC 10261 BP. Besides, as a lectic, RCA recognizing asialo α1-acid glycoprotein is preferable to be utilized.

The present invention provides a diagnostic strip for immunochromatography which comprises a monoclonal antibody binding only with asialo α1-acid glycoprotein and excluding heptoglobin and α2-macroglobulin; and lectin RCA recognizing asialo glycoprotein; measure the concentration of asialo α1-acid glycoprotein in a test sample; and diagnose a liver disease rapidly and easily.

Preferably, the present invention provides the diagnostic strip for immunochromatography which includes the monoclonal antibody As 16.89 deposited with the accession number KCTC 10261 BP and RCA as a lectin. The diagnostic strip for immunochromatography of the present invention comprises glass fiber (GF) membrane coated with micro-particles such as gold-colloid conjugated with nonoclonal antibody; nitrocellulose membrane (NC) in which RCA band is lined as a diagnostic line and an monoclonal antibody band as a standard line; a sample pad absorbing test sample solution; an absorbent pad discarding non-reactive substance; and an adhesive plastic backing for mounting the above-mentioned members.

The diagnostic strip for immunochromatography of the present invention is mounted in due turn, preferably NC membrane, GF membrane, a sample pad and absorbent pad are partially overlaid onto the adhesive plastic backing to transfer substance smoothly by capillary reaction.

The diagnostic strip for immunochromatography can be prepared by the conventional procedure. Preferably, the diagnostic strip of the present invention can be manufactured to a cassette type or a stick type.

Besides, the test sample is preferable to be blood or serum and 10-fold diluted by using elution buffer and the elution buffer is preferable to be 50 mM borate buffer containing 5% sucrose, 1% bovine serum albumin or 1% Triton X-100.

The diagnostic strip for immunochromatography of the present invention is used to detect a liver disease as follows: when a test sample is diluted and dropped onto the sample pad, both the standard line and diagnostic line are colored on the strip after 3~5 minutes so that the sample be judged according to colors whether positive for hepatic disease or not. Precisely, if Ab-gold conjugate is adopted as a microparticle, the positive sample including asialo α1-acid glycoprotein reveals red color both on the standard line and the criteria line after a test and the negative sample including asialo α1-acid glycoprotein in a normal level (not a patient of liver disease) reveals red color only on the standard line.

As described above, the diagnostic strip for immunochromatography of the present invention can detect asialo α1-acid glycoprotein to reach a cutoff value, about 1.50 μg/ml, which can diagnose a liver disease early and monitor its prognosis and treatment if the level of asialo α1-acid glycoprotein present in patients of liver cirrhosis and liver cancer continued to be evaluated.

Furthermore as illustrated above, the monoclonal antibody which reacts only with asialo α1-acid glycoprotein and excludes heptoglobin and α2-macroglobulin and the diagnostic strip for immunochromatography by using the same can inform the test result rapidly and conveniently so that liver diseases can be diagnosed easily. Therefore, it is expected to contribute to the prevention and treatment of liver diseases.

EXAMPLES

Practical and presently preferred embodiments of the present invention are illustrated as shown in the following Examples. However, it will be appreciated that those skilled in the art, on consideration of this disclosure, may make modifications and improvements within the spirit and scope of the present invention.

Example 1

Separation and Purification of Asialo α1-acid Glycoprotein (AsAGP)

α1-acid glycoprotein (AGP) was separated and purified from asialo glycoprotein contained in human blood plasma as follows.

Figure 1:
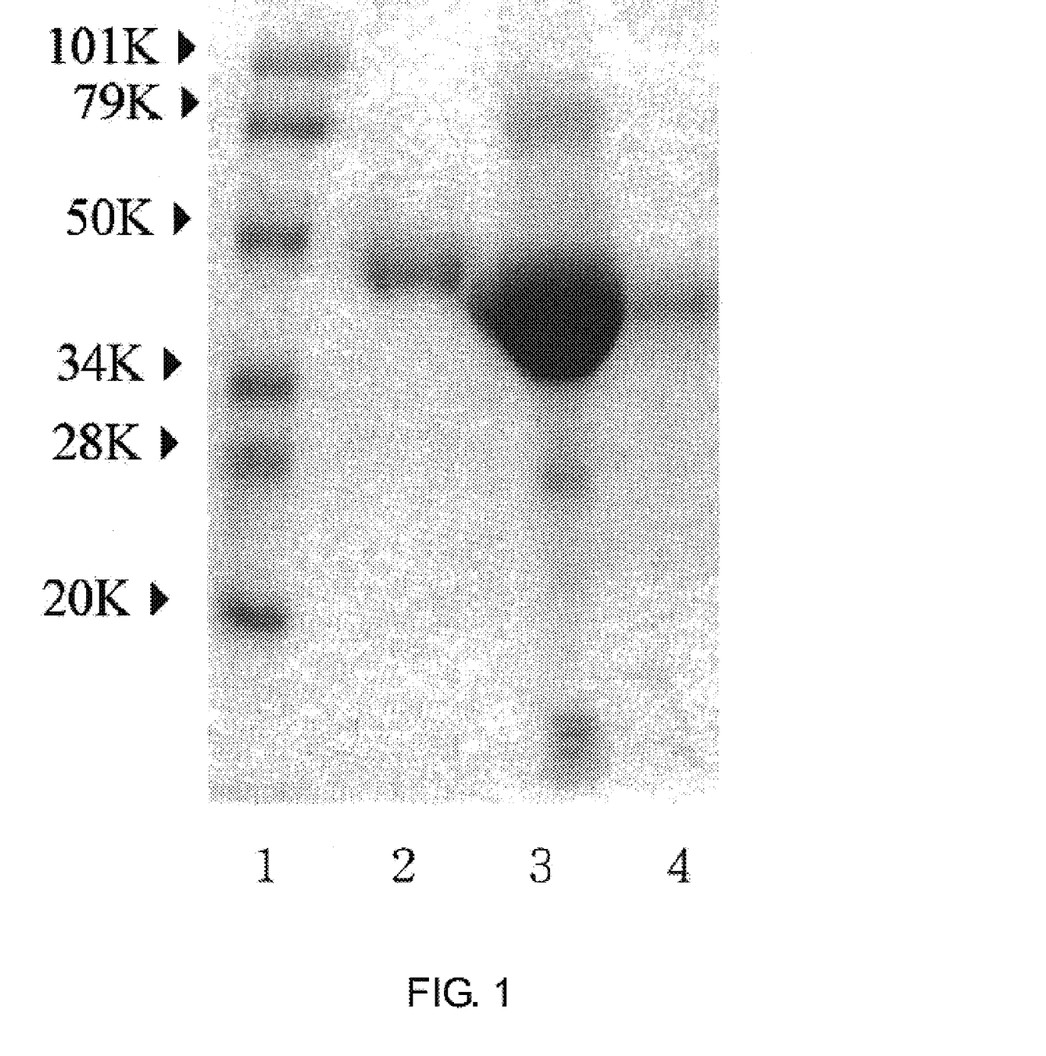
FIG. 1 depicts α1-acid glycoprotein (AGP) and desialylated α1-acid glycoprotein purified from blood plasma by performing sodium dodecyl polyacrylamide gel electrophoresis (SDS-PAGE).

2 NIH unit of thrombin was added to 200 ml of human blood plasma, stored at 37° C. for 2 hours and at 4° C. overnight and centrifuged to remove blood clot. The serum prepared above was dialyzed by using 0.05M of sodium acetate buffer (pH 4.3), loaded onto DEAE column previously equilibrated by using the same buffer, and then eluted through linear concentration gradient after 0.05 M of sodium acetate buffer (pH 4.3) and 0.1 M of sodium acetate buffer (pH 4.3) were mixed. Afterward, the optical density (OD) was measured at 280 nm and the data was illustrated in FIG. 1. The fractions including AGP and other proteins were collected, mixed with ammonium sulfate to 0.5 g/ml and centrifuged to precipitate proteins. The resulting supernatant was mixed again with ammonium sulfate to 0.18 g/ml to precipitate proteins and the pellet was dissolved in a small amount of distilled water (D.W.), dialyzed sufficiently by using D.W. and then lyophilized.

40 mg of AGP separated above was hydrolyzed at 80° C. for 2 hours by using 6 ml of 0.1 N sulfate solution, neutralized by using 1 N of sodium hydroxide and then dialyzed by using 0.01 N of phosphate buffer (pH 7.4). The desialylated α1-acid glycoprotein (AsAGP) prepared in the above procedure was loaded onto Sephadex G-200 column, filtrated by using 0.01 M of phosphate buffer. (pH 7.4) and calculated through OD value at 280 nm and finally the fractions including proteins were collected. The result was illustrated in FIG. 1: lane 1 is the standard marker of protein molecular weight; lane 2 is α1-acid glycoprotein; lane 3 and 4 are asialo α1-acid glycoprotein (AsAGP).

Example 2

Preparation of Monoclonal Antibody Against Asialo α1-acid Glycoprotein

Immunization of Mice

In order to obtain an immunized mouse essential to prepare a hybridoma cell line producing a monoclonal antibody against asialo α1-acid glycoprotein, asialo α1-acid glycoprotein as an antigen was suspended well by using Titer-MAX, adjusted to 50 μg/50 ml of concentration and then injected into peritoneal cavity of Balb/c mice aged 6~8 weeks. After 2 weeks, the same amount of antigen mentioned in the first injection was mixed with Titer-MAX and injected repeatedly onto the same site. Through the same procedure, the antigen was injected again after 7 days and repeatedly injected after 3 weeks. Afterward, the small amount of blood was collected from a tail of mouse and examined to evaluate a titer.

(2) Cell Fusion

In order to perform cell fusion for preparing a hybridoma cell line, mice were immunized with asialo α1-acid glycoprotein antigen mentioned above and spleen cells and myeloma cells were collected from the mice. Then, $10^8$ of spleen cell and $10^7$ myeloma cell (SP2/0) were washed sufficiently, mixed together and 1 ml of PEG 1500 was poured for about 1 minutes, stirred slightly for about 1 minutes. Afterward, 9 ml of RPMI medium was added for about 3 minutes to reach 50 ml of final volume as stirred slowly. The cell suspension was centrifuged to collect the cell pellet, suspended again to $1\sim2\times10^5$ cells/ml by using HAT medium, poured into a 96-well microplate in 0.2 ml volume per well, and then incubated at 37° C. in $CO_2$ incubator.

Screening of Hybridoma Cell Producing Monoclonal Antibody

In order to select a hybridoma cell specific for asialo α1-acid glycoprotein, ELISA method was tried by exploiting a microplate coated with asialo α1-acid glycoprotein as follows. Precisely, asialo α1-acid glycoprotein antigen was put into a microplate in 100 μl (1 μg/ml) per well to coat the surface and washed off to remove antigens not reacted. The culture medium of hybridoma cell was poured to each well in 100 μl, reacted for 2 hours and washed off by using Tween 20 phosphate buffer (PBST) to remove the culture medium not reacted. Afterward, goat anti-mouse IgG-horseradish peroxidase (HRP) was added, reacted for an hour at room temperature and washed off by using PBST solution. Then, ortho-phenylenediamine (OPD) was utilized as a substrate of peroxidase, reacted and examined to measure OD value at 490 nm with ELISA reader.

As a result, the cell line secreting antibodies highly binding to asialo α1-acid glycoprotein antigen was first screened and repeatedly selected to separate the hybridoma cell secreting a monoclonal antibody specific for asialo α1-acid glycoprotein antigen. The resulting cells were treated by the limiting dilution to become a monoclone and the hybridoma cell line producing a monoclonal antibody was sorted again. Afterward, 2 clones having the highest titer such as asialo α1-acid glycoprotein 1 and asialo α1-acid glycoprotein 2 were collected, tried to measure the titer of supernatant in culture medium through ELISA method and then the subunit type of the monoclonal antibody was analyzed by the double immunodiffusion. Consequently, the antibodies secreted from the clones of the present invention were identified as $IgG_1$ and IgM respectively.

The cell line secreting $IgG_1$ has been named as AS 16.89 and deposited to Korea Research Institute of Bioscience and Biotechnology, Gene Bank in May 24, 2004 (accession number KCTC 10261 BP).

Large Scale Production and Purification of Monoclonal Antibody

In order to produce a monoclonal antibody from a hybridoma cell in a large scale, 0.5 ml of pristane was injected into peritoneal cavity of Balb/c mice. After 1 week, each cell line obtained in the above procedure (3) was injected to the experimental mice in 5×10⁶ cells per mouse and then peritoneal fluid was collected from the peritoneal cavity if swollen. The peritoneal fluid was centrifuged at 12,000 rpm to collect cells and the resulting supernatant was filtrated through protein G column to separate and purify the monoclonal antibody against asialo α1-acid glycoprotein and also stored at −20° C. for the next experiments.

Identification of Specificity of Monoclonal Antibody by Western Blot

Figure 2:
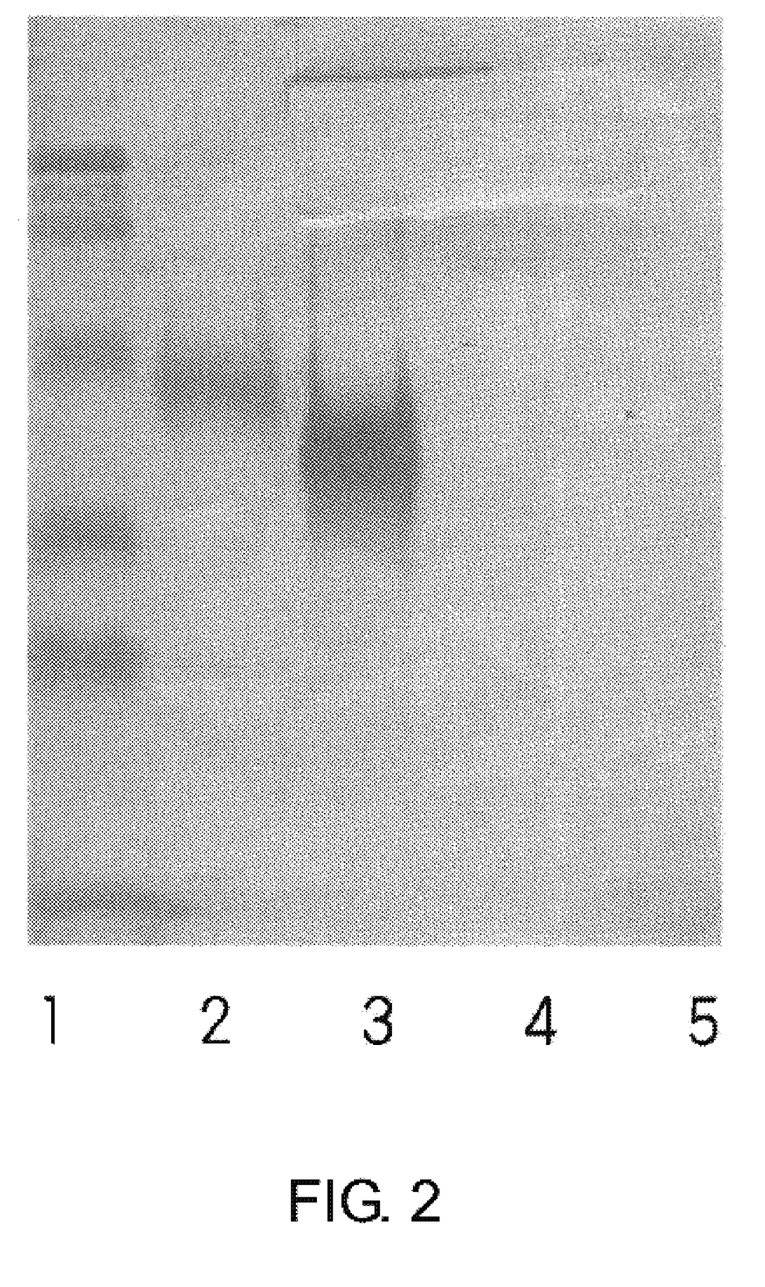
FIG. 2 depicts the monoclonal antibody against asialo α1-acid glycoprotein produced from the hybridoma cell line of the present invention by performing western blotting.

In order to elucidate the property of monoclonal antibody specific for asialo α1-acid glycoprotein, the monoclonal antibody against asialo α1-acid glycoprotein purified through the above-mentioned procedure (4) was identified by performing SDS-polyacrylamide gel electrophoresis and western blotting (See FIG. 2). The western blotting was accomplished by a typical procedure in the prior arts. In FIG. 2, lane 1 is a standard marker of protein molecular weight; lane 2, α1-acid glycoprotein; lane 3, asialo α1-acid glycoprotein; lane 4, α2-macroglobulin; and lane 5, heptoglobin.

Figure 3:
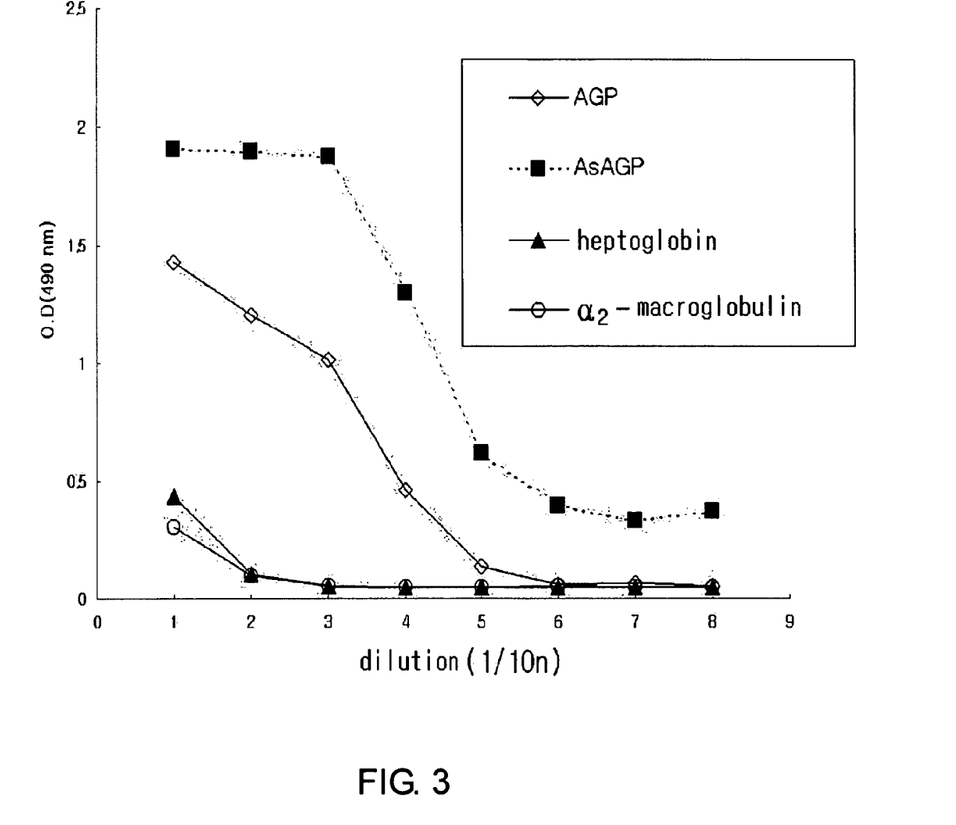
FIG. 3 depicts the monoclonal antibody prepared in the present invention by performing ELISA method, which reacts only with asialo α1-acid glycoprotein and excludes heptoglobin and α2-macroglobulin.

Identification of Specificity of Monoclonal Antibody by Enzyme Immunochemical Assay Asialo α1-acid glycoprotein, heptoglobin, α2-macroglobulin antigen were added to 96-well microplate in 100 μl (1 μg/ml) per well respectively, attached on the surface, reacted for 2 hours with the monoclonal antibody against asialo α1-acid glycoprotein as added in 100 μl, and washed off by using phosphate buffer-Tween 20 (PBST) to remove the culture medium not reacted. Further, goat anti-mouse IgG-HRP was added, reacted for an hour at room temperature and washed sufficiently by using PBST solution. Afterward, ortho-phenylenediamine (OPD) was added as a substrate of peroxidase and reacted so as to measure OD value at 490 nm with ELISA reader. As a result, it is confirmed that the monoclonal antibody against asialo α1-acid glycoprotein purified above be the monoclonal antibody specific for asialo α1-acid glycoprotein (See FIG. 3). In FIG. 3, AGP depicts α1-acid glycoprotein and AsAGP, asialo α1-acid glycoprotein of the present invention.

Example 3

Detection of Liver Disease by Diagnostic Kit for Immunochromatography

The diagnostic kit for immunochromatography of the present invention which can measure the concentration of asialo α1-acid glycoprotein in a test sample by the immune reaction between the monoclonal antibody As 16.89 specific for asialo α1-acid glycoprotein produced above and asialo α1-acid glycoprotein in blood was manufactured and applied in clinical fields as follows.

Preparation of Diagnostic Kit for Immunochromatography

The diagnostic kit for detecting asialo α1-acid glycoprotein in blood is composed of following components as described below.

monoclonal antibody (As16.89) specific for asialo α1-acid glycoprotein fixed onto solid carrier such as microplate lectin (RCA)-horseradish peroxidase (HRP) against asialo α1-acid glycoprotein sample dilution buffer (1% BSA/PBST)

enzyme substrate solution (OPD)

washing buffer (PBST)

standard solution of asialo α1-acid glycoprotein stopping buffer

Measurement a. The standard solution (1 μg/ml) of asialo α1-acid glycoprotein was poured in 100 μl respectively to microplate on which the monoclonal antibody As 16.89 was fixed. Experiment samples, including 40 normal persons, 155 patients without liver disease, 36 patients of acute hepatitis, 272 patients of chronic hepatitis (CH), 230 patients of liver cirrhosis, 72 patients of hepatocarcinoma (HCC) proceeded from liver cirrhosis, were obtained from St. Mary Hospital, Catholic Medical School. The blood sample was diluted to 1:10 ratio by using the dilution buffer, allotted onto each well of microplate in 100 μl and incubated for 120 minutes at room temperature.

b. After reacted, the washing buffer was added in 100 μl per well and washed three times repeatedly.

c. The lectin (RCA)-HRP diluted by the process for the preparation was allotted onto each well of microplate and reacted for 60 minutes at room temperature.

d. Step b was repeated.

e. The enzyme substrate solution (OPD) was allotted onto each well of microplate above.

f. The stopping buffer was added on each well in 100 μl to stop the enzymatic reaction.

g. OD value was measured at 490 nm with ELISA reader.

As a result, the content of asialo α1-acid glycoprotein in blood was evaluated through the above-mentioned procedure as illustrated in Table 1.

TABLE 1

Measurement of blood AsAGP (cutoff value: 1.50 μg/ml)

| class | | sum | Ave. + SD μg/ml* | AsAGP > 1.50 μg/ml No. of sample | % | AsAGP > 1.50 μg/ml No. of sample | % |
|---|---|---|---|---|---|---|---|
| standard group | sum | 196 | 0.89 × 0.46 | 19 | 10.0 | 177 | 90 |
| | normal | 41 | 0.84 × 0.41 | 2 | 5 | 39 | 95 |
| | non-hepatic disease | 155 | 0.90 × 0.48 | 17 | 11 | 138 | 89 |
| Group 1 of liver disease | acute hepatitis | 36 | 1.33 × 0.77 | 9 | 25 | 27 | 75 |
| Group 2 of liver disease | sum | 574 | 2.48 × 0.89 | 323 | 56 | 251 | 44 |
| | chronic hepatitis (CH) | 272 | 1.63 × 0.45 | 99 | 36 | 173 | 64 |
| | liver cirrhosis (LC) | 230 | 3.12 × 0.42 | 165 | 72 | 65 | 28 |
| | hepatocarcinoma (HCC) with liver cirrhosis (LC) | 72 | 3.64 × 0.1 | 59 | 82 | 13 | 18 |

Consequently, it is confirmed that the concentration of asialo α1-acid glycoprotein (AsAGP) for normal persons and patients of non-hepatic disease be below 1.00 μg/ml in an average level and the number of sample over 1.50 μg/ml in the concentration of AsAGP be about 10%. In patient groups of acute hepatitis, chronic hepatitis, liver cirrhosis and hepatocarcinoma with liver cirrhosis, the blood level of AsAGP was evaluated to average 1.33 μg/ml, 1.63 μg/ml, 3.12 μg/ml and 3.64 μg/ml respectively. The concentrations be remarkably distinguished from those of standard group, even if the ratio of sample over 1.5 μg/ml of AsAGP be 25%, 36%, 72% and 82% respectively. Therefore, it is verified that this test be effective upon the diagnosis of hepatic diseases.

Hence, according to data demonstrated above, the cutoff value for diagnosing a liver disease was decided to be 1.50 μg/ml when the monoclonal antibody As 16.89 of the present invention was used for the enzyme immunoassay.

Example 4

Preparation of Diagnostic Strip for Immunochromatography

Preparation of Monoclonal Antibody-gold Conjugate

The monoclonal antibody specific for asialo α1-acid glycoprotein selected in the present invention was added in 15 μg/ml to the colloidal solution of gold particles, reacted for 2 hours at room temperature and rotated. Then, 10% of BSA was blended in 1/10 volume to become 1% of concentration and again reacted for an hour to prepare Ab-gold conjugate. Afterward, the resultant was centrifuged at 12,000 rpm for 40 minutes to discard the supernatant solution and 2 mM of borate buffer was added to wash off Ab-gold conjugate. The resultant was washed repeatedly, three times and finally 2 mM of borate buffer containing 1% BSA was added in about 1/10 volume of gold solution and suspended. After measured with UV spectrometer, the OD value at 530 nm was adjusted to 3.00 by dilution.

Sample Pad

The sample pad is a member absorbing test sample and is made of cellulose material for this purpose.

Glass Fiber (GF) Membrane

The glass fiber is a component on which AsAGP in test sample and the monoclonal antibody prepared by the process of the present invention are reacted. The GF membrane was coated with gold colloid particle-As 16.89 on the surface and prepared as follows. The monoclonal antibody produced from hybridoma cell line As 16.89 of the present invention was conjugated onto the membrane as illustrated in step (1).

GF membrane (1.0 cm×0.7 cm) purchased from Millipore Co. Ltd. was soaked by using 20 mM sodium borate buffer, sprayed uniformly by using gold colloid particle-As 16.89 onto the surface, dried at 37° C. and thus made to GF membrane pad for immunochromatography (also conjugate pad) on which a monoclonal antibody conjugated with a coloring particle is fixed.

Nitrocellulose (NC) Membrane and Lining

Nitrocellulose membrane purchased from Millipore Co. Ltd. was cut to a proper size (0.7 cm×5 cm), lined at a point of about 3.4 cm from the bottom of plastic backing with goat anti-mouse IgG as a standard line and at a point of 2.7 cm as a criteria line for detecting asialo α1-acid glycoprotein by using RCA purchased from EY Lab, and then dried to complete the NC membrane.

Absorbent Pad

Cellulose membrane was used to absorb substance not reacted in a test sample after an immune reaction and to transfer the sample solution through capillary reaction.

Preparation of Diagnostic Strip for Immunochromatography

Figure 4A:
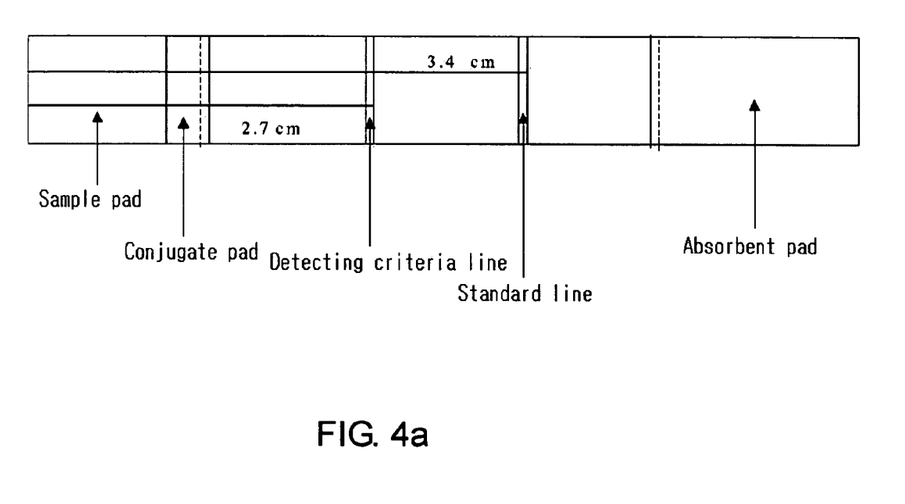
FIG. 4a depicts a planar view of the diagnostic strip for immunochromatography prepared in the present invention.
Figure 4B:
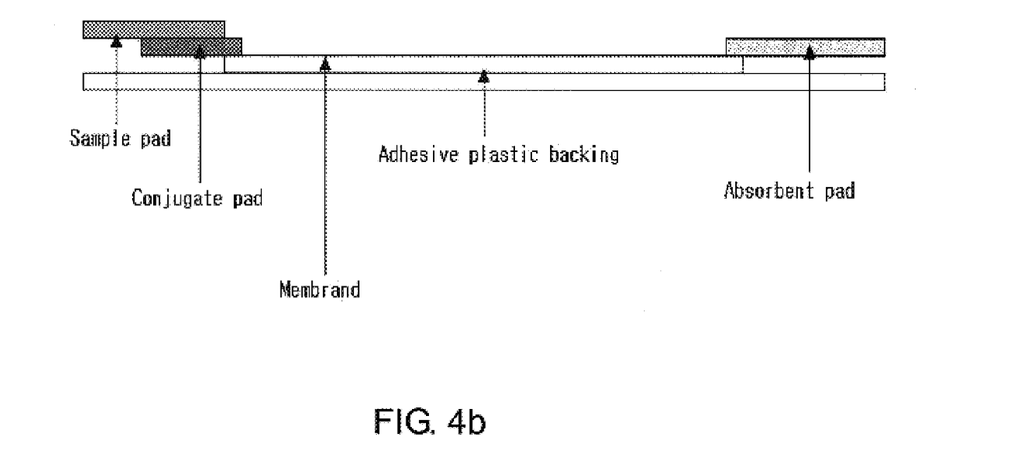
FIG. 4b depicts a front view of the diagnostic strip for immunochromatography prepared in the present invention.

As illustrated in FIG. 4a and FIG. 4b, the above-mentioned members were mounted onto the adhesive plastic backing. Precisely, NC membrane, GF membrane, sample pad and absorbent pad were arranged in due turn, overlaid evenly in about 0.1 cm portion and fixed by adhesion in order to transfer substance smoothly through capillary reaction.

Example 5

Analysis of Asialo α1-acid Glycoprotein by Using Diagnostic Strip for Immunochromatography Serum sample was diluted to 1:10 ratio by using elution buffer (such as 50 mM borate buffer containing 5% sucrose, 1% bovine serum albumin or 1% Triton X-100) and added in 60~70 μl volume onto the sample pad of diagnostic strip for immunochromatography prepared in Example 4 so as to examine the standard line and the criteria line after 3~5 minutes whether colored or not.

Figure 5:
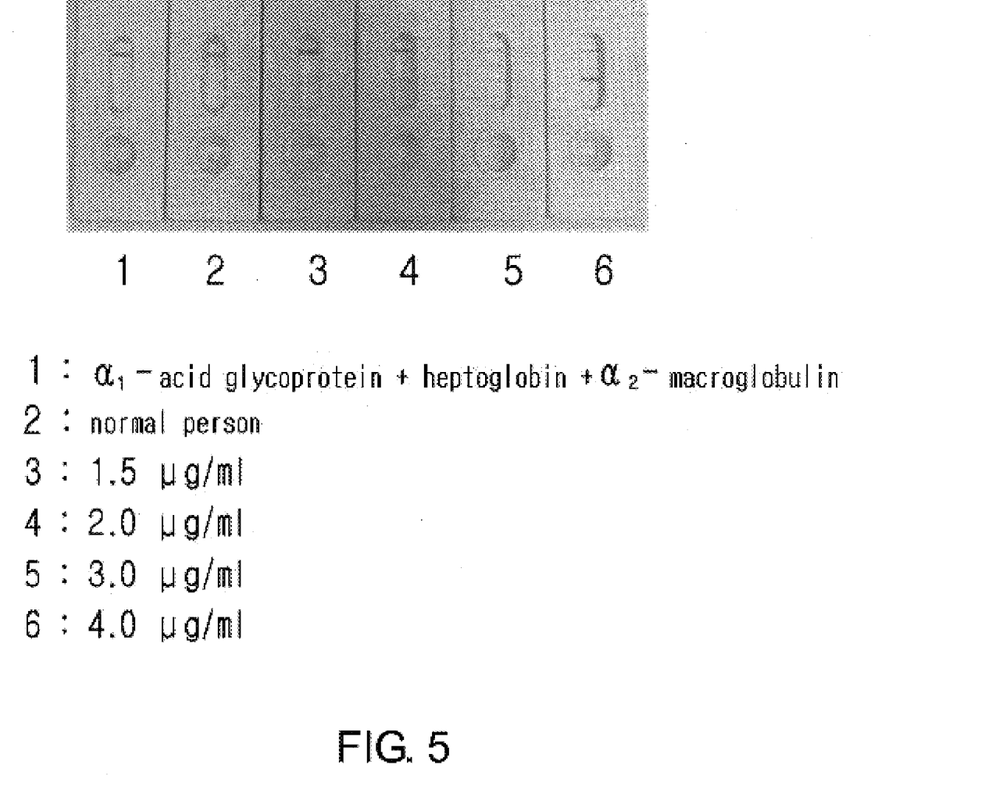
FIG. 5 depicts the result which is measured by using the cassette type diagnostic strip for immunochromatography prepared in the present invention and indicates asialo α1-acid glycoprotein in a concentration-dependent mode.

FIG. 5 depicts the result from the cassette type strip for immunochromatography. NO. 1 is the standard dropping the mixture of α1-acid glycoprotein (AGP), heptoglobin and α2-macroglobulin; NO. 2, the diagnostic strip in the serum of normal person; NO. 3~NO. 6, the strip in 1.5 μg/ml, 2.0 μg/ml, 3.0 μg/ml and 4.0 μg/ml of asialo α1-acid glycoprotein respectively. As illustrated in FIG. 5, in NO. 3, the line is obscure; and in NO. 4~NO. 6, red colors are clear both on the standard line (upper) and the criteria line (lower).

The diagnostic strip for immunochromatography of the present invention is observed that only the standard line become red in the test sample of normal person (negative) under the cutoff value, 1.50 μg/ml of asialo α1-acid glycoprotein since antigen-antibody-enzyme conjugate complex was not formed. On the other hand, when asialo α1-acid glycoprotein level increased to more than 1.50 μg/ml due to a liver disease, both the lines become red, in which asialo α1-acid glycoprotein was absorbed on the sample pad, reacted with gold particle-monoclonal antibody As 16.89 conjugate on GF membrane to form an immune complex, transferred onto NC membrane through capillary reaction and conjugated with RCA in the criteria line on NC membrane to make gold precipitate. Furthermore, the criteria line can be varied in thickness and color density, depending upon the concentration of asialo α1-acid glycoprotein. Therefore, it is possible to predict the severity of liver disease by the concentration of asialo α1-acid glycoprotein in the test sample.

INDUSTRIAL APPLICABILITY

As illustrated above, the monoclonal antibody specific for asialo α1-acid glycoprotein and the diagnostic strip and the diagnostic kit for immunochromatography by using the same of the present invention can be utilized to evaluate asialo α1-acid glycoprotein present in blood sample rapidly and easily. Therefore, the monoclonal antibody and the diagnostic device of the present invention can monitor the severity, the treatment and the prognosis of liver diseases efficiently.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A method for diagnosing liver disease selected from a group consisting of chronic hepatitis, liver cirrhosis and hepatocarcinoma with liver cirrhosis, comprising:

contacting a monoclonal antibody which reacts only with asialo α1-acid glycoprotein and does not react with heptoglobin and α2-macroglobulin and lectin RCA (*Ricinus communis* agglutinin) recognizing asialo glycoprotein with a test sample to measure an amount of asialo α1-acid glycoprotein (AsAGP), in which the monoclonal antibody is the subclass $IgG_1$ produced from the mouse cell line deposited with the Korea Research Institute of Bioscience and Biotechnology having accession number KCTC 10261 BP;

measuring an amount of complexes formed between the antibody and AsAGP in the test sample; and relating a measured amount of AsAGP in the test sample to a diagnosis of whether the test sample is from a person having the liver disease, wherein the liver disease is selected from the group consisting of chronic hepatitis, liver cirrhosis and hepatocarcinoma with liver cirrhosis, and wherein a cutoff value for diagnosing that the test sample is from the person having said liver disease is above 1.50 λg/ml.

2. The method for diagnosing a liver disease according to claim 1, in which the test sample is blood or serum.

* * * * *